United States Patent [19]

Zimble

[11] Patent Number: 5,022,856
[45] Date of Patent: Jun. 11, 1991

[54] DENTAL PROBE ASSEMBLY

[76] Inventor: Alan Zimble, 2006 Limestone Rd., Ste. 2, Wilmington, Del. 19808

[21] Appl. No.: 426,006

[22] Filed: Oct. 24, 1989

Related U.S. Application Data

[63] Continuation-in-part of Ser. No. 236,773, Aug. 26, 1988, Pat. No. 4,883,425.

[51] Int. Cl.$^5$ .............................................. A61C 19/04
[52] U.S. Cl. ........................................ 433/72; 433/29; 433/32; 128/776
[58] Field of Search ....................... 433/32, 29, 72, 75; 128/776, 777; 33/513, 514

[56] References Cited

U.S. PATENT DOCUMENTS 4,501,555  2/1985  Ditchburn ............................. 433/29
4,790,751  12/1988  Reinhardt et al. ..................... 433/29

FOREIGN PATENT DOCUMENTS 8403143  8/1984  PCT Int'l Appl. ................... 433/72
8605382  9/1986  PCT Int'l Appl. ................... 433/72

Primary Examiner—Cary E. Stone
Attorney, Agent, or Firm—Connolly & Hutz

[57] ABSTRACT

A dental probe assembly includes a tool having a handle portion at one end thereof and a portion detachably connected to the handle. A probe tip is mounted to the neck portion. The probe tip is a disposable light conducting and emitting member. Light is transmitted to the probe tip. The tool also transmits the amount of light emitted by the probe tip. In use, the probe tip would be inserted into a gum pocket and the amount of light would be sensed which would correspond to the length of the probe tip outside of the pocket. This value would be compared with a standard value which corresponds to the full length of the probe tip and the comparison would indicate the depth of the pocket.

17 Claims, 1 Drawing Sheet

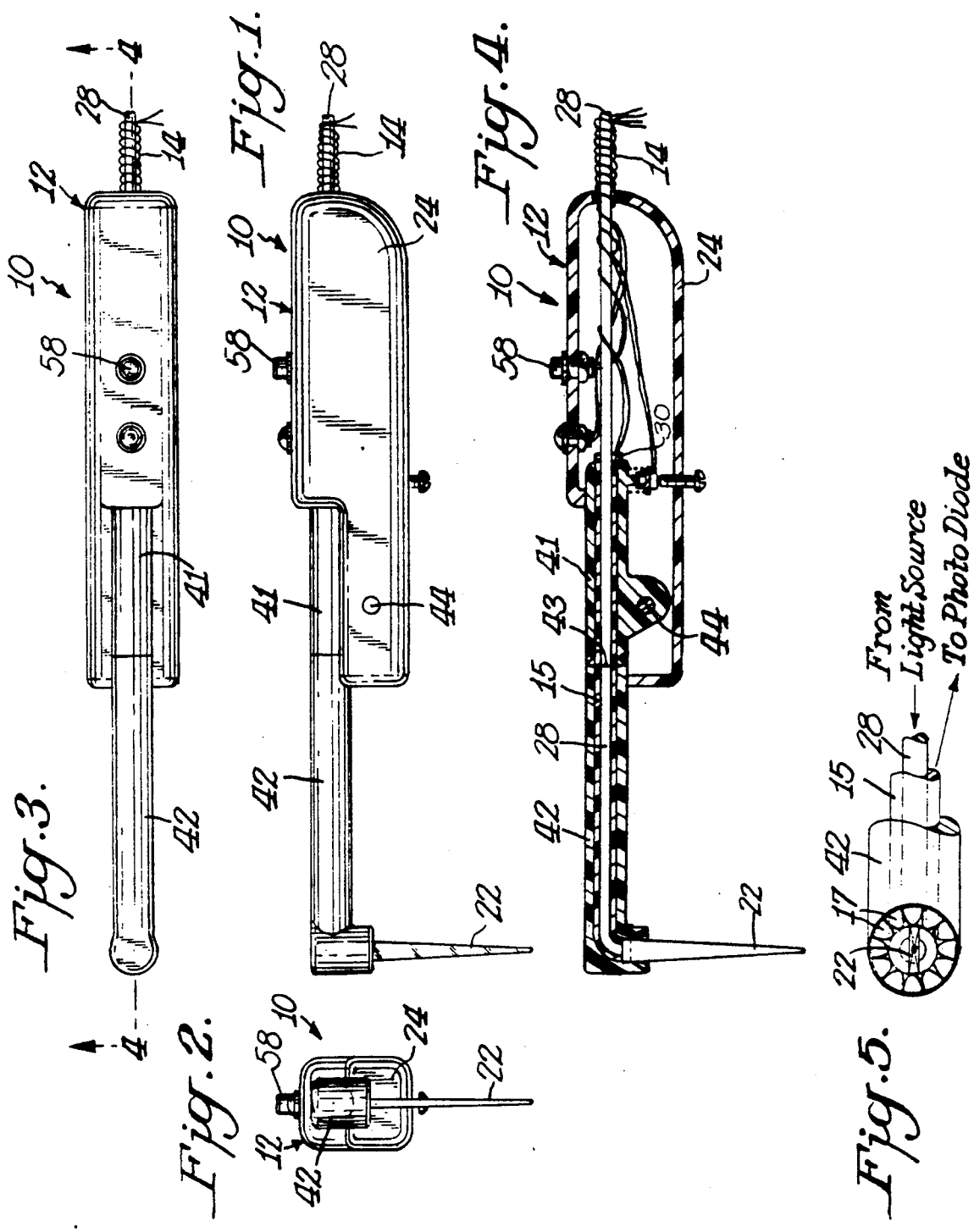

DENTAL PROBE ASSEMBLY

CROSS-REFERENCE TO RELATED APPLICATION

This application is a continuation-in-part of application Ser. No. 236,773 filed Aug. 26, 1988 now U.S. Pat. No. 4,883,425.

BACKGROUND OF INVENTION

Various devices exist for measuring the depth of a gum pocket in periodontal or other dental treatments. These devices generally include inserting some form of probe into the pocket and having a scale associated with the probe so as to measure the depth of the pocket. Such devices are of varying reliability because their effectiveness depends to a great extent upon requiring a uniform force from measurement to measurement in inserting the probe into the pocket where manual pressure is used to apply that force. The reading is usually visually taken and manually applied by the operator. As a result, there is a virtual certainity that uniform and reliable results will not be obtained. The margin of error is reported to be ±2-3 mm.

SUMMARY OF INVENTION

An object of this invention is to provide a dental probe assembly which automatically, accurately and reliably measures the depth of a gum pocket.

In accordance with this invention, the dental probe assembly includes a tool having a handle portion at one end with a neck portion detachably connected to the handle portion and with the probe tip extending from the neck portion. The detachable connection permits the detached portion to be sterilized, thereby providing the device with the capability of multiple use and at the same time providing excellent protection in the transmission of infectious diseases such as hepatitis and aids.

In a preferred embodiment of this invention a probe tip is a light conducting and emitting member associated with a first fiber optic bundle. A second fiber optic bundle is concentrically arranged around the first fiber optic bundle and communicates with lenses arranged around the base of the probe tip to gather light and transmit the light by the fiber optic bundle back to a photodiode within the handle portion. A comparative readings may be actuated by a manual switch or by a voice recognition switch or may be automatically taken.

THE DRAWINGS

FIG. 1 is a side elevation view of a dental probe assembly in accordance with this invention;

FIG. 2 is a front elevation view of the assembly shown in FIG. 1;

FIG. 3 is a top plan view of the assembly shown in FIGS. 1-2;

FIG. 4 is a cross-sectional view taken through FIG. 3 along the line 4—4; and

FIG. 5 is a bottom plan view of the front portion of the probe shown in FIGS. 1-4.

DETAILED DESCRIPTION

The present invention relates to modifications of the dental probe assembly disclosed in parent application Ser. No. 236,773 filed Aug. 26, 1988. The details of that application are incorporated herein by reference thereto. For the sake of simplicity the details of the parent application will only be referred to as is necessary for an understanding of the present invention. In general, the parent application involves a probe assembly wherein the depth of a pocket, particularly, a gum pocket is determined by the utilization of a probe tip made from a light conducting and emitting member. Light is conducted to the probe tip and a first reading is made outside of the pocket to provide a comparative value which would correspond to the full length of the probe tip. The probe tip is then inserted into the pocket and a second reading is made when light is transmitted to the probe tip to provide a value corresponding to the length of the probe tip outside of the pocket. A comparison of these readings is used for indicating the depth of the pocket.

As illustrated, the dental probe assembly 10 includes a hand held portable tool 12 connected by wiring 14 and fiber optic bundle 28 to a computer (not shown), as described in the parent application. A neck portion 42 extends from the handle portion 24 with a probe tip 22 being detachably mounted to neck portion 42. Probe tip 22 is made of a uniform light conducting and emitting material, such as a plastic material which has light transmitted thereto in any suitable manner and preferably by fiber optic bundle 28 so that probe tip 22 is illuminated.

Tool 12 also includes an optical sensing section which comprises a photodiode 30. FIG. 4 illustrates the photodiode to be mounted within the handle section 24. Light is conducted to the photodiode 30 by means of a second fiber optic bundle 15 which is arranged concentrically around fiber optic bundle 28. Fiber optic bundle 15 communicates at its remote end with a series of lenses 17 as best shown in FIG. 5, designed to read emissions of the probe and ambient light in the vicinity of the probe. When a reading is to be taken of the amount of light on probe tip 22 a switch 58 is actuated. The light is transmitted through fiber optic bundle 28 to probe tip 22. The light is sensed by lenses 17 and conducted back to fiber optic bundle 15 to photodiode 30, for the taking of a measurement of that light. If probe tip 22 is not inserted in the pocket, the reading will indicate the full length of probe tip 22 after having automatically nulled out ambient light and this reading will provide a comparison reading. A second reading would be taken when probe tip 22 is inserted fully into the pocket and the reading will indicate the amount of light resulting from the length of probe tip 22 being outside of the pocket nulling out ambient light. This second reading would be compared with the first reading to provide an indication of the depth of the pocket.

In accordance with one aspect of the invention the switch for actuating the readings may be a manual switch 58 as described in the parent application. Alternatively, the switch 58 may activate a voice recognition device as is known in the art which would be capable of following basic commands and thus able to make corrections or deletions during a program for reading the depths of a series of pockets. The readings may automatically be taken. Additionally, it is noted that the drawings illustrate the communication within the tool 12 to be by means of electrical wiring 14. The invention, however, may be practiced by using FM frequency transmission to free the device from motion limiting cable attachments.

A significant feature of the invention is that neck section 42 is detachably connected to handle section 24. The line of detachable connection is indicated in the drawings by the reference numeral 43. The exposed portion of neck section 42 is connected to an intermediate section 41 which remains mounted to handle section 24. Intermediate section 41 would include pivot pin 44 so that the connected neck 41,42 can pivot in the manner described in the parent application. It is noted that a variation of the present application from the parent application is that neck section 41,42 is straight rather than being curved. The neck section can be stiffly flexible, similar to a goose neck lamp, so that it can be bent to a desired position to redirect to probe tip and will remain in that position while the readings are taken.

Any suitable form of detachable connection may be used such as a snap on connection or a bayonet lock provided that upon connection, the necessary elements, such as the fiber optic bundles and physical structure of the neck section are in firm contact and proper communication with each other. As noted in the parent application, the invention may be practiced for measuring the depth of any pocket, but in its preferred use the invention measures the depth of gum pockets.

A significant advantage in the detachable connection of neck portion 42 to the handle portion is that the detachable mounting permits sterilization including autoclaving and microwaving to provide for multiple use of the sterilized components without requiring the handle section to be sterilized.

What is claimed is:

1. A probe assembly for depth measurement comprising a hand held portable tool having a handle section at one end thereof, a neck section detachably mounted to said handle section, a probe tip mounted to said neck section remote from said handle section, said probe tip being made of a light conducting and emitting material, means for transmitting light to said probe tip, means for indicating the amount of light on said probe tip to thereby indicate the depth of a pocket into which said probe tip is inserted, said means for transmitting light to said probe tip comprising first fiber optic bundle in said handle section and said neck section associated with said probe tip, and said indicating means includes a second fiber optic bundle in said handle section and said tool section communicating with a lens assembly located at said probe tip.

2. The assembly of claim 1 wherein said second fiber optic bundle is concentrically arranged around said first fiber optic bundle.

3. The assembly of claim 1 wherein said neck portion is a straight portion in line with said handle portion.

4. The assembly of claim 1 wherein said portion is made from a stiffly flexible material.

5. The assembly of claim 1 wherein said probe tip is a dental probe tip detachably mounted to said neck portion.

6. A probe assembly for depth measurement comprising a hand held portable tool having a handle section at one end thereof, a neck section detachably mounted to said handle section, a probe tip mounted to said neck section remote from said handle section, said probe tip being made of a light conducting and emitting material, means for transmitting light to said probe tip, means for indicating the amount of light on said probe tip to thereby indicate the depth of a pocket into which said probe tip is inserted, and said neck portion being connected to a pivot assembly within said handle portion.

7. A probe assembly for depth measurement comprising a hand held portable tool having a handle section at one end thereof, a neck section detachably mounted to said handle section, a probe tip mounted to said neck section remote from said handle section, said probe tip being made of a light conducting and emitting material, means for transmitting light to said probe tip, means for indicating the amount of light on said probe tip to thereby indicate the depth of a pocket into which said probe tip is inserted, said indicating means including means for nulling out the ambient light and measuring the amount of light of said probe tip just before and just after said probe tip is inserted into the pocket, and actuating means on said handle section for actuating said indicating means.

8. The assembly of claim 7 wherein said actuating means includes a manual switch.

9. The assembly of claim 7 wherein said actuating means includes a voice recognition device.

10. The assembly of claim 7 wherein said actuating means is automatically actuated.

11. A probe assembly for depth measurement comprising a hand held portable tool having a handle section at one end thereof a neck section connected to and extending from said handle section, a probe tip mounted to said neck section remote from said handle section, sad probe tip being made a light conducting and emitting material, a first fibre optic bundle in said handle section and said neck section communicating with said probe tip for transmitting light to said probe tip, a lens assembly connected to said neck section at said probe tip, and a second fiber optic bundle associated with said lens assembly and extending into said neck section and said handle section for indicating the amount of light on said probe tip whereby the depth of a pocket could be determined in accordance with the amount of light on said probe tip.

12. The assembly of claim 11 wherein said second fiber optic bundle is arranged concentrically arranged around said first fiber optic bundle.

13. The assembly of claim 12 including a photodiode in said handle section, and said second fiber optic bundle communicating with said photodiode.

14. The assembly of claim 13 including indicating means for nulling out the ambient light and measuring the amount of said light just before and just after said probe tip is inserted into the pocket, and actuating means on said handle section for actuating said indicating means.

15. The assembly of claim 14 wherein said actuating means includes a manual switch.

16. The assembly of claim 14 wherein said actuating means includes a voice recognition device.

17. The assembly of claim 14 wherein said actuating means is automatically actuated.

* * * * *